United States Patent [19]
Goldenberg et al.

[11] Patent Number: 5,637,288
[45] Date of Patent: Jun. 10, 1997

[54] CHIMERIC ANTIBODY FOR DETECTION AND THERAPY OF INFECTIOUS AND INFLAMMATORY LESIONS

[75] Inventors: David M. Goldenberg, Short Hills; Hans J. Hansen, Mystic Island, both of N.J.

[73] Assignee: Immunomedics, Inc., Morris Plains, N.J.

[21] Appl. No.: 457,134

[22] Filed: Jun. 1, 1995

Related U.S. Application Data

[63] Continuation of Ser. No. 446,546, Dec. 5, 1989.

[51] Int. Cl.⁶ .................................................. A61K 39/395
[52] U.S. Cl. .................... 424/1.49; 424/1.11; 424/9.3; 424/153.1; 424/182.1; 424/178.1
[58] Field of Search .......................... 424/178.1, 101.1, 424/182.1, 153.1, 1.49, 9.3

[56] References Cited

U.S. PATENT DOCUMENTS

| | | | |
|---|---|---|---|
| 4,671,958 | 6/1987 | Rodwell et al. | 424/85 |
| 4,925,648 | 5/1990 | Hansen et al. | 424/1.11 |
| 4,926,869 | 5/1990 | Rubin et al. | 128/654 |

OTHER PUBLICATIONS

Skubitz et al., The Journal of Immunology, 131(5):1882–1887, 1983.
Waldmann, Science, 252:1657, 1991.
Oi et al., Biotechniques, 4(3):214, 1986.
Morrison et al., Science, 229:1202, 1985.
Roitt et al., Immunology, 2.12–2.13, 1985.
Harris et al., TibTech, 11:42, 1993.
Abramowicz et al., The New England Journal of Medicine, 736, 1992.
Morrison et al. Clin Chem 34/9 1668–1675 (1988).

*Primary Examiner*—Lila Feisee
*Assistant Examiner*—Julie E. Reeves
*Attorney, Agent, or Firm*—Foley & Lardner

[57] ABSTRACT

A chimeric antibody-agent conjugate for targeting foci of leukocyte accretion comprises a recombinant chimera having an antigen-binding hypervariable region which binds specifically to granulocytes, and a constant region of a human immunoglobulin having an Fc portion with high affinity for receptors on human mononuclear lymphoid cells, said chimera being conjugated to at least one diagnostic agent or therapeutic agent.

A method for targeting an imaging or therapy agent to an inflammatory or infectious lesion comprises injecting a mammal parenterally with an effective amount for targeting of the above chimeric anti-leukocyte conjugate.

9 Claims, No Drawings

CHIMERIC ANTIBODY FOR DETECTION AND THERAPY OF INFECTIOUS AND INFLAMMATORY LESIONS

This application is a continuation of application Ser. No. 07/446,546, filed Dec. 5, 1989.

BACKGROUND OF THE INVENTION

This invention relates to a chimeric antibody and a method for its use in targeting at least one diagnostic or therapeutic agent to an inflammatory or infectious lesion. The chimeric antibody includes an antigen-binding variable region that specifically binds to an epitope on human granulocytes and a constant region having an Fc portion that has a high affinity for receptors on human mononuclear lymphoid cells. Such chimeric antibodies are conjugated to a suitable diagnostic label or therapeutic agent for targeting to sites of infection or inflammation.

The value of labeling granulocytes with radionuclides to detect occult infection and inflammation has been appreciated for some time. Granulocytes, mononuclear blood cells and platelets have been labeled by incubation with various In-111 salts or simple In-111 organic ligands. This method requires isolation of the cells from blood prior to labeling and is laborious and time-consuming.

More recently, it has been demonstrated that radiolabeled murine anti-granulocyte antibodies are also effective for imaging occult infections, as an alternative to pre-labeled granulocytes. The labeled antibodies can be injected directly into the vascular system, eliminating the need for the laborious task of cell isolation. In U.S. Pat. No. 4,634,586 (Goodwin et al.), incorporated herein by reference in its entirety, leukocytes are radioimmunoimaged by injecting patients with an immunoreactive nonleukocidal conjugate of an anti-leukocyte monospecific antibody and a gamma emitting radioactive metal chelate, waiting for the conjugate to localize on the leukocytes, injecting a patient with an antibody to the conjugate to clear the blood of background nonlocalized conjugate, and visualizing the leukocytes by scintillation scanning.

It is also known that radiolabeled human polyclonal IgG can be used to image occult infection and inflammation. These antibodies appear to localize at such sites due to interaction of the Fc moiety of a subpopulation of the radiolabeled IgG with mononuclear cells present at the disease site.

The problem that limits the optimal practice of the use of antibodies to granulocytes to detect occult infection or inflammation is the fact that as the disease process is contained, the granulocyte population in the lesion is reduced and replaced by mononuclear lymphoid cells (MLC's), i.e., monocytes, T-cells, B-cells and/or nonspecific killer cells (NK-cells), that appear to bear high affinity Fc-receptors. The ratio of granulocytes to MLC's can also vary markedly as a function of the type of infectious agent which initiates the lesion. Thus, anti-granulocyte antibodies will not be as effective for imaging later stages of infection or inflammation as earlier, more acute stages or for imaging lesions having a low granulocyte level for other reasons.

Moreover, it has been found that nonspecific IgG also localizes in certain types of cancers (see, e.g., Rubin et al., N. Eng. J. Med., 321:935–940, 1989) so that the granulocyte specificity of the conjugate of the present invention permits better descrimination between cancerous and non-cancerous legions.

Leukocyte imaging has been severely limited in the prior art due to poor target to background ratio. It has been shown that the localization ratio can be increased, for example, by using second antibody clearance. However, the target to background ratio remains a problem when using a mixture of anti-leukocyte antibodies because each targeting antibody normally binds to a specific leukocyte cell type, either a granulocyte, a monocyte, a B-lymphocyte or a T-lymphocyte. Therefore, there will be many antibodies that are highly reactive and specific for a particular leukocyte cell in the background that have not bound to the target site, because that particular leukocyte cell type is not present at significant levels at the site of infection or inflammation.

One solution to the foregoing problems is disclosed in applicants' copending and commonly assigned patent application, Hansen et al., U.S. Ser. No. 07/226,180, filed July 29, 1988 (issued as U.S. Pat. No. 4,925,648 on May 15, 1990), which is incorporated by reference herein in its entirety. That application discloses a polyspecific antibody composite conjugate having affinity for more than one type of leukocyte. A diagnostic or therapeutic agent targeted with such a conjugate will be localized to the lesion with lesser dependence upon the particular type of leukocyte which predominates at the site of the lesion.

There is a need for alternative or extended solutions to these problems.

OBJECTS OF THE INVENTION

One object of the present invention is to provide a chimeric antibody-agent conjugate which selectively binds to granulocytes and also to a different type of lymphocyte, and which can be used for targeting inflammatory or infectious lesions.

A further object of the present invention is to provide a method for targeting a diagnostic or therapeutic agent to an infectious or inflammatory lesion with an enhanced target to background ratio.

Other objects of the present invention will become more apparent to those of ordinary skill in the art in light of the following discussion.

SUMMARY OF THE INVENTION

These and other objects of the present invention are achieved by providing a chimeric antibody-agent conjugate for targeting foci of leukocyte accretion, comprising a recombinant chimera having an antigen-binding hypervariable region which binds specifically to granulocytes, and a constant region of a human immunoglobulin having an Fc portion with high affinity for receptors on human mononuclear lymphoid cells, said chimera being conjugated to at least one diagnostic agent or therapeutic agent.

The invention also provides a method for targeting a diagnostic or therapeutic agent to an inflammatory or infectious lesion which comprises injecting a mammal parenterally with an effective amount for targeting of one or more of the foregoing chimeric antibody-agent conjugates.

In addition, the present invention provides sterile injectable preparations and kits for use in practicing the foregoing method.

DETAILED DESCRIPTION OF THE INVENTION

The present invention provides an improvement over the prior art imaging method of Goodwin et al. and an extension of the Hansen et al. '180 method through the use of a chimeric antibody-agent conjugate for targeting foci of leukocyte accretion.

T-cells, B-cells, granulocytes and monocytes that are involved in the development of an infectious or inflammatory lesion are often present in markedly different ratios in the inflammatory or infectious lesion, depending upon the nature of the agent that initiates the development of the lesion and/or on the age of the lesion. Use of a monospecific antibody, as taught by Goodwin, will result in inefficient targeting of the lesion if only a portion of the leukocyte population at the site of the lesion bind the targeting antibody, and this will reduce the target to background ratio (also called "localization ratio"). Use of a mixture of antibodies with different leukocyte specificities can slightly improve the percentage of injected dose reaching the target site if the right proportion of specificities is used, but can further increase binding to non-target leukocytes if the lesion contains primarily a single leukocyte cell type.

The present invention resolves this dilemma by using a chimeric targeting antibody which is able to bind to at least two different leukocyte cell types. The imaging agent component of the antibody-agent conjugate is thereby localized at the target site with higher efficiency and an enhanced target to background ratio, regardless of the ratios of the various types of leukocytes.

The chimeric targeting antibody component of the antibody-agent conjugate of the invention can be made by a number of different techniques that are by now well known in the art.

Anti-granulocyte monoclonal antibodies (Mabs) can be produced in non-human mammals, e.g., mice, rats, rabbits, goats or the like, and isolated DNA encoding all, but preferably only the essential antigen-binding region, of the hypervariable domains of such Mabs is incorporated in DNA encoding the remainder of a human immunoglobulin. The production of such a chimeric human Mab involves excising the DNA sequences coding for all or part of one or both of the heavy and light variable regions of a mammalian Mab and introducing it by known methods into human immunoglobulin DNA lacking that region. The isolated DNA can then be cloned into suitable vectors and expressed in host cells, e.g., *E coli* or cultured mammalian myeloma cells, which are then selected based on their production of chimeric human Mabs that bind to granulocytes. Expression of such Mabs can be accomplished using known methods (see, e.g., Ausubel et al, Eds., CURRENT PROTOCOLS IN MOLECULAR BIOLOGY, Wiley Interscience, New York, 1987, 1989, §§ 1.1–6.8.) in cells such as *E. coli* (see, e.g., Riechmann et al., Nature, 332:323–327, 1988; Ward et al., Nature, 341:544–546, 1989) or transfected murine myeloma cells (see, e.g, Morrison, Science, 229:1202–1210, 1986; Sahagan et al., J. Immunol., 137:1066–1074, 1986; Gillies et al., Biotechnol., 7:799–804, 1989; Nakatani et al., Biotechnol., 7:805–810, 1989).

Mabs that recognize and bind to granulocyte epitopes are available commercially or may be made from somatic cell hybridization techniques described originally by Kohler, B. and Milstein, C., Nature (1975) 256:495–497 and reviewed at length in Monoclonal Antibodies, Kennett, T. J., et al, eds, Plenum (1980). Antibodies to human granulocyte antigens may be made by inoculating a host, e.g., mice, rabbits, goats, baboons or other mammalian species, with human granulocytes or membrane preparations therefrom. Splenocytes may be taken from the immunized host and fused with a suitable myeloma cell line using the above mentioned somatic cell hybridization techniques to produce hybridomas that produce anti-granulocyte antibodies. These hybridomas may be isolated, subcloned and cultivated to produce monoclonal antibodies.

Some anti-granulocyte Mabs are available commercially. For example, the catalogue of Immunotech (Marseilles, France, with worldwide distribution including Pel Freeze, Brown Deer, Wis., USA) lists commercially available anti-granulocyte Mabs, many of which are suitable for use in preparing chimeras according to the present invention. Certain of the antibodies bind to epitopes common to more than one type of leukocyte, e.g., monocytes and granulocytes, B-cells and granulocytes, T-cells and granulocytes. The antibodies produced and distributed by Immunotech are similar to other antibodies from clones available elsewhere. Commercially available anti-granulocyte Mabs are typically of murine or rat origin and typically are IgGs or IgMs, although suitable antibodies for use in preparing conjugates according to the invention are not intended to be limited as regards species or Ig class.

Certain anti-T-cell antibodies are useful for the present invention, particularly an antibody that binds to both monocyte and granulocyte antigens, i.e., a monoclonal which binds to the CDW14 antigen. The CD antigens are leukocyte determinants that define antibodies having particular leukocyte specificities. A pair of antibodies that bind to the same epitope on the same CD antigen will cross-block binding to the same leukocyte cell types. It is contemplated that a polyspecific chimera can be produced using the hypervariable region of an antibody that specifically binds to an antigen common to granulocytes and, e.g., T-cells, B-cells, NK-cells and/or monocytes. The principle is the same, however, of incorporating in a single chimera a specific antigen binding region from an antibody that targets granulocytes (and optionally also monocytes, T-cells, B-cells and/or NK-cells), and an Fc portion or protein segment thereof with a high affinity for receptors on MLC's. The resultant targeting chimera will target foci of infection or inflammation more effectively because of the multiple binding specificities in a single targeting molecule, but also because lesions with multiple and variable amounts of lymphocytes will be targeted and a lower percentage of the injected dose of targeting conjugate will be retained in non-lesion background due to the presence of leukocytes in normal tissue near the site of the lesion.

It is within the skill of the art to excise smaller portions of the gene for the recombinant chimera described above, such that segments retaining significant binding affinity for granulocytes and segments having a high affinity for receptors on MLC's are combined and expressed as a smaller protein having substantially equivalent targeting function to the chimera. Such "trimmed" chimeric proteins are included in the scope of the term "chimeric antibody" as used in the context of the present invention.

Gene segments coding for immunoglobulin-like protein fragments having a high binding affinity for granulocytes and other leukocytes can be combined, along with a segment coding for one or more receptor-binding Fc protein sequences of a human immunoglobulin idiotype or isotype, in a single recombinant DNA which directs the expression of a polyspecific (i.e., trispecific or more) targeting molecule for carrying a diagnostic and/or therapeutic agent to a focus of infection or inflammation.

The DNA used to produce the chimera can come from any human immunoglobulin-producing cells known to produce immunoglobulin having a high affinity for receptors on human MLC's, as tested, e.g., by immunofluorescence. Polyclonal human antiserum having high affinity for MLC's is known. See, e.g., Fischman et al., J. Nucl. Med., 30:1095–1100, 1989; Rubin et al., J. Nuc. Med., 30:385–389, 1989. Such antiserum can be further purified by passage through affinity colums with bound MLC's, and then recovered and isolated.

The use of a chimeric "human" or "humanized" antibody in the present invention is motivated by the presence on the Fc portion of certain human immunoglobulin isotypes of regions that show high binding affinity to "Fc receptor" regions on certain populations or subpopulations of human mononuclear lymphoid cells. Ideally, a wholly human monoclonal anti-granulocyte antibody would serve this purpose, but the present state of the art is such that production of stable human monoclonal antibody-producing cell lines is difficult and often unreliable. Nevertheless, future developments may make production of such human monoclonals possible and reliable, and these human monoclonals are clearly to be contemplated as equivalent to chimeras for production of conjugates according to the invention.

According to one emerging method for making human Mabs, either whole human granulocytes or, preferably, membrane component fractions from such cells, are introduced into a severe-combined immunodeficient (SCID) mouse which has been repopulated with human lymphoid cells, in order to hyperimmunize the human lymphoid cells present in the mouse. See, e.g., Mosier et al, Nature, 335:256–9 (1988). The hyperimmunized cells are then isolated and cultured as immortalized cells, e.g., by Epstein-Barr virus (EBV) infection, and then fused to human myeloma cells to produce hybridomas. See, e.g., James et al., J. Immunol. Meth., 100:5–40 (1987). The resulting hybridomas are then screened, using, e.g., flow cytometry, to select hybridomas producing antibodies that bind to human granulocytes. Once a hybridoma is selected that produces useful quantities of an anti-granulocyte Mab, the culture supernatant is used as a source for purifying and recovering a pharmaceutically acceptable Mab by known methods. To the extent that a stable human Mab can be produced by such a technique or varient thereof, it will be an appropriate targeting component of a conjugate according to the invention.

The immunological profile of the antibodies used to make the chimeric conjugate of the present invention can be adjusted to ensure optimal binding to infectious or inflammatory lesions and minimal binding to nontarget sites. Depending upon the diagnostic or therapeutic use to which the conjugate is to be put, the mix of leukocyte cell type specificities, antigen specificities and specificities for epitopes on antigens present on particular cell types, as well as of binding constants for the target antigens and/or cell types, all can be used to fine tune the selectivity and targeting efficiency of the reagent according to the invention. This is advantageous in minimizing the cost to the patient as well as the amount of radiation to which the patient must be subjected, an important consideration in radioimmunotherapy.

It is generally desirable to use chimeric antibodies having a relatively high immunoreactivity, i.e., a binding constant of at least about $10^5$ l/mole, preferably at least about $10^7$ l/mole, and high immunospecificity, i.e. at least about 40%, preferably at least about 60%, more preferably at least about 70–95% for granocyte epitopes.

It may be preferable for certain applications to use antibodies having a somewhat lower binding constant in the present invention. Antibodies with high binding constants are likely to bind tightly not only to leukocytes at the site of inflammation or infection, but also to leukocytes present in the circulatory system, the marrow or normal tissues. On the other hand, antibodies with a lower binding constant will tend to accrete mainly at concentrated leukocyte foci at the site of a lesion, by virtue of a type of mass action effect. This will reduce premature clearance and nontarget accretion of the imaging label or, in therapy applications to be described below, the therapeutic agent, and thus increase the effective amount for targeting the lesion.

Chimeric antibody conjugates according to the present invention advantageously can target, i.e., monocytes and granulocytes for the diagnosis and treatment of osteomyelitis; T-cells, B-cells, monocytes or granulocytes for the diagnosis and treatment of chronic infection; Ia(dr) histocompatibility antigen and granulocytes for the treatment of fever of unknown origin, e.g., granulomatous infections, tubercular lesions, fungal infections and like.

The target sites can be any infectious lesion, inflammatory deposit or occult lesion having leukocytes, present in a relatively concentrated focus. Localization of lesions containing leukocytes will occur directly through reactivity of the antibody-agent conjugate with the leukocytes resident in the lesion at the time of parenteral administration as well as through entry of labeled leukocytes into the lesion.

The chimeric targeting antibody can be labeled with, or conjugated or adapted for conjugation to, a radioisotope for scintigraphic imaging or a magnetic resonance image enhancing agent, for use as a diagnostic imaging agent. Suitable imaging radiosotopes include, e.g., gamma-emitters, positron-emitters and x-ray emitters. Suitable and convenient radioisotopes for labeling antibodies include, but are not limited to, Iodine-131, Iodine-123, Indium-111, Gallium-67, Technetium-99m and Fluorine-18.

Any conventional method of radiolabeling which is suitable for labeling proteins for in vivo use will be generally suitable for labeling the chimera. This can be achieved by direct labeling with, e.g., a radioisotope of a halogen or a metal ion, using conventional techniques or more sophisticated methodologies, or by attaching a chelator for a radiometal or paramagnetic ion. Such chelators and their modes of attachment to antibodies are well known to the ordinary skilled artisan and are disclosed inter alia in, e.g., Childs et al., J. Nuc. Med., 26:293 (1985); and in Goldenberg U.S. Pat. Nos. 4,331,647, 4,348,376, 4,361,544, 4,468,457, 4,444,744, and 4,624,846. Typical are derivatives of ethylenediaminetetraacetic acid (EDTA) and diethylenetriaminepentaacetic acid (DPTA). These typically have groups on the side chain by which the chelator can be attached to an antibody. Alternatively, carboxyl or amine groups on a chelator can be activated and then coupled to a chimeric antibody by well known methods. For example, deferoxamine, which is a chelator for Ga-67 has a free amine group that can be activated with a suitable linker to contain an activated carboxyl, isothiocyanate or like group, and then coupled to amines on an antibody.

The chelator may be bound to the chimeric antibody, directly or through a short or long chain linker moiety, through one or more functional groups on the antibody, e.g., amine, carboxyl, phenyl, thiol or hydroxyl groups. Various conventional linkers can be used, e.g., diisocyanates, diisothiocyanates, carbodiimides, bis-hydroxysuccinimide esters, maleimide-hydroxysuccinimide esters, glutaraldehyde and the like, preferably a selective sequential linker such as the anhydride-isothiocyanate linker disclosed in U.S. Pat. No. 4,680,338.

Labeling with either Iodine-131 (I-131) or Iodine-123 (I-123) is readily effected using an oxidative procedure wherein a mixture of radioactive potassium or sodium iodide and the antibody is treated with chloramine-T, e.g., as reported by Greenwood et al, Biochem. J., 89, 114 (1963) and modified by McConahey et al, Int. Arch. Allergy Appl. Immunol., 29, 185 (1969). This results in direct substitution of iodine atoms for hydrogen atoms on the antibody molecule, presumably on tyrosine residues, possibly also on tryptophan and even on phenylalanine residues, depending on the proportions of reagents and the reaction conditions. Alternatively, lactoperoxidase iodination may be used, as described by Feteanu, supra, page 303, and references cited therein.

Some more advanced methods of labeling are disclosed in pending applications U.S. Ser. Nos. 742,436 (Jun. 7, 1985), 084,544 (Aug. 12, 1987), and 176,421 (Apr. 1, 1988). The disclosures of all of the foregoing patents and applications are incorporated herein in their entireties by reference. A wide range of labeling techniques are disclosed in Feteanu, "Labeled Antibodies in Biology and Medicine", pages 214–309 (McGraw-Hill Int. Book Co., New York et al, 1978). The introduction of various metal radioisotopes may be accomplished according to the procedures of Wagner et al., J. Nucl. Med., 20,428 (1979); Sundberg et al, J. Med. Chem., 17, 1304 (1974); and Saha et al. J. Nucl. Med., 6, 542 (1976). The foregoing are merely illustrative of the many methods of radiolabeling proteins known to the art.

Examples of compounds useful for MRI image enhancement include paramagnetic ions, e.g., Gd(III), Eu(III), Dy(III), Pr(III), Pa(IV), Mn(II), Cr(III), Co(III), Fe(III), Cu(II), Ni(II), Ti(III) and V(IV) ions, or radicals, e.g., nitroxides, and these would be conjugated to a substrate bearing paramagnetic ion chelators or exposed chelating functional groups, e.g., SH, $NH_2$, COOH, for the ions, or linkers for the radical addends. The MRI enhancing agent must be present in sufficient amounts to enable detection by an external camera, using magnetic field strengths which are reasonably attainable and compatible with patient safety and instrumental design. The requirements for such agents are well known in the art for those agents which have their effect upon water molecules in the medium, and are disclosed, inter alia, in, e.g., Pykett, Scientific American, 246:78 (1982); and Runge et al., Am.J. Radiol., 141:1209 (1987).

It is well understood that many of the same methods for introducing metals, directly or in the form of chelates, into antibodies will be suitable for introduction of MRI agents into the chimeric antibody of the invention to form imaging agents for infectious lesions. MRI agents advantageously have a large number of paramagnetic ions or radicals for enhanced imaging. One method for introducing a plurality of such ions is to load a carrier polymer with chelates and link the carrier to the antibody, preferably site-specifically at a site remote from the antigen binding sites and the Fc receptor binding site of the chimera. This has the advantage that larger numbers of chelators can be attached to the antibody at fewer sites on the antibody B itself, so that immunoreactivity is not as seriously compromised. Examples of polymers that are useful for loading the antibody with chelator include, e.g., polyols, polysaccharides, polypeptides and the like. See U.S. Pat. No. 4,699,784 (Shih et al.) and U.S. Pat. No. 4,046,722 (Rowland). One type of polysaccharide is dextran. The chelator can be functionalized to contain reactive groups towards the dextran hydroxyls, e.g., anhydrides, isocyanates or isothiocyanates and the like. Alternatively, dextran can be derivatized in a number of ways, e.g., by conversion to an aminodextran. It will be appreciated that similar methods will be useful for loading a plurality of drug molecules on an antibody or antibody composite, as will be discussed more fully hereinafter.

The process for preparing an antibody conjugate with an aminodextran (AD) carrier normally starts with a dextran polymer, advantageously a dextran of average molecular weight (MW) of about 10,000–100,000, preferably about 10,000–40,000, and more preferably about 15,000. The dextran is then reacted with an oxidizing agent to effect a controlled oxidation of a portion of its carbohydrate rings to generate aldehyde groups. The oxidation is conveniently effected with glycolytic chemical reagents, e.g., $NaIO_4$, according to conventional procedures.

It is convenient to adjust the amount of oxidizing agent so that about 50–150, preferably 100 aldehyde groups are generated, for a dextran of MW of about 40,000, with about the same proportion of aldehyde groups for other MW dextrans. A larger number of aldehyde groups, and subsequent amine groups, is less advantageous because the polymer then behaves more like polylysine. A lower number results in less desirable loading of the chelator or boron addend, which may be disadvantageous.

The oxidized dextran is then reacted with a polyamine, preferably a diamine, and more preferably a mono- or poly-hydroxy diamine. Suitable amines include, e.g., ethylenediamine, propylenediamine or similar polymethylenediamines, diethylenetriamine or like polyamines, 1,3-diamino-2-hydroxypropane or other like hydroxylated diamines or polyamines, and the like. An excess of the amine relative to the aldehyde groups can be used, to insure substantially complete conversion of the aldehyde functions to Schiff base (imine) groups.

Reductive stabilization of the resultant intermediate is effected by reacting the Schiff base intermediate with a reducing agent, e.g., $NaBH_4$, $NaBH_3CN$, or the like. An excess of the reducing agent is used to assure substantially complete reduction of the imine groups to secondary amine groups, and reduction of any unreacted aldehyde groups to hydroxyl groups. The resultant adduct can be further purified by passage through a conventional sizing column to remove cross-linked dextrans. An estimate of the primary number of available amino groups on the AD can be effected by reaction of a weighed sample with trinitrobenzenesulfonic acid and correlation of the optical density at 420 nm with a standard. This method normally results in essentially complete conversion of the calculated number of aldehyde groups to primary amine groups on the AD.

Alternatively, the dextran can be derivatized by conventional methods for introducing amine functions, e.g., by reaction with cyanogen bromide, followed by reaction with a diamine. The AD should be reacted with a derivative of the particular drug or chelator, in an activated form, preferably a carboxyl-activated derivative, prepared by conventional means, e.g., using dicyclohexylcarbodiimide (DCC) or a water soluble variant thereof.

The scintigraphic imaging method of the invention is practiced by injecting a mammal, preferably a human, parenterally with an effective amount for scintigraphic imaging of the radiolabeled chimeric anti-leukocyte antibody. By parenterally is meant, e.g. intravenously, intraarterially, intrathecally, intramuscularly, interstitially or intracavitarily. It is contemplated that a subject will receive a dosage of from about 1 mCi to 50 mCi of radiolabeled conjugate, the amount being a function of the particular radioisotope and mode of administration. Suitable gamma-emitting isotopes include, e.g., I-131, I-123, Tc-99m, In-111 and Ga-67, the foregoing being illustrative of radioisotopes emitting in the range of 50–500 KeV. For intravenous injection, the amounts are normally: about 2–10 mCi, preferably about 2–5 mCi, of I-131; about 5–10 mCi, preferably about 8 mCi, of I-123; about 10–40 mCi, preferably about 20 mCi of Tc-99m; about 2–5 mCi, preferably about 4 mCi of In-111 or Ga-67.

The radiolabeled chimeric anti-leukocyte antibody is conveniently provided as an injectable preparation for mammalian use, preferably a sterile injectable preparation for human use, for targeting a scintigraphic imaging agent to an infectious or inflammatory lesion containing leukocytes, preferably comprising: a sterile injectable solution containing an effective amount of the radiolabeled composite in a pharmaceutically acceptable sterile injection vehicle, preferably phosphate-buffered saline (PBS) at physiological pH and concentration. Other conventional pharmaceutically acceptable vehicles may be utilized as required for the site of parenteral administration.

A representative preparation to be parenterally administered in accordance with this invention will normally contain about 0.1 to 20 mg, preferably about 2 mg, of radiolabeled chimeric antibody, in a sterile solution which advantageously also contains, e.g., about 10 mg of human serum albumin (1% USP: Parke-Davis) per milliliter of 0.04M phosphate buffer (pH 7.4 Bioware) containing 0.9% sodium chloride.

Once enough isotope has deposited at the target site, scanning is effected with either a conventional planar and/or SPECT gamma camera, or by use of a hand held gamma probe used externally or internally to localize the inflammation or the lesion. The scintigram is normally taken by a gamma imaging camera having one or more windows for detection of energies in the 50–500 KeV range. Use of radioisotopes with high energy beta or positron emissions is also possible and would entail use of imaging cameras with the appropriate detectors, all of which are conventional in the art.

Magnetic resonance imaging (MRI) is effected in an analogous method to scintigraphic imaging except that the imaging agents will contain MRI enhancing species rather than radioisotopes. It will be appreciated that the magnetic resonance phenomenon operates on a different principle from scintigraphy. Normally the signal generated is correlated with the relaxation times of the magnetic moments of protons in the nuclei of the hydrogen atoms of water molecules in the region to be imaged. The magnetic resonance image enhancing agent acts by increasing the rate of relaxation, thereby increasing the contrast between water molecules in the region where the imaging agent accretes and water molecules elsewhere in the body. However, the effect of the agent is to increase both $T_1$, and $T_2$, the former resulting in greater contrast, while the latter results in lesser contrast. Accordingly the phenomenon is concentration-dependent, and there is normally an optimum concentration of a paramagnetic species for maximum efficacy. The optimum concentration will vary with the particular agent used, the locus of imaging, the mode of imaging, i.e., spin-echo, saturation-recovery, inversion-recovery and for various other strongly $T_1$ dependent or $T_2$ dependent imaging techniques, and the composition of the medium in which the agent is dissolved or suspended. These factors, and their relative importance are known in the art. See, e.g., Pykett, op.cit., and Runge et al., op.cit.

The MRI method of the invention is practiced by injecting a mammal, preferably a human, parenterally with an effective amount for magnetic resonance imaging of a conjugate according to the present invention of a chimeric anti-leukocyte antibody and an MRI enhancing agent. It is contemplated that a subject will receive a dosage of labeled conjugate sufficient to enhance the MRI signal at the site of a lesion by at least about 20%, preferably 50–500%, the amount being a function of the particular paramagnetic species and the mode of administration.

Again, the labeled conjugate is conveniently provided as an injectable preparation for mammalian use, preferably a sterile injectable preparation for human use, for targeting an MRI agent to an infectious or inflammatory lesion containing leukocytes, preferably comprising: a sterile injectable solution containing an effective amount of the labeled chimera in a pharmaceutically acceptable sterile injection vehicle, preferably phosphate-buffered saline (PBS) at physiological pH and concentration. Other conventional pharmaceutically acceptable vehicles for parenteral administration may be utilized as required for the site of parenteral administration.

A representative preparation to be parenterally administered in accordance with this invention will normally contain about 0.1 to 20 mg, preferably about 2 mg, of labeled chimeric antibody, in a sterile solution which advantageously also contains, e.g., about 10 mg of human serum albumin (1% USP: Parke-Davis) per milliliter of 0.04M phosphate buffer (pH 7.4 Bioware) containing 0.9% sodium chloride. Once enough of the MRI agent has deposited at the target site, scanning is effected with a conventional MRI camera camera to image the lesion.

In a preferred embodiment of this invention, the localization ratio of the primary labeled chimeric antibody-agent conjugate is enhanced through the use of a nonlabeled second antibody to scavenge non-targeted circulating conjugate and promote its clearance, as disclosed for related imaging agents in Goldenberg, U.S. Pat. No. 4,624,846, the disclosure of which is incorporated herein in its entirety by reference. This technique is likewise applicable to the chimeric anti-leukocyte antibody conjugated to a therapeutic agent, as will be discussed hereinafter. The term "localization ratio" is utilized in its conventional sense, i.e. the ratio of target to nontarget antibody conjugate. In general, the second antibody is used in an amount that will enhance the localization ratio of the primary antibody conjugate by at least about 20 percent and typically by 50 percent or more.

The second antibody may be whole IgG or IgM, or a fragment of IgG or IgM, so long as it is capable of binding the primary antibody conjugate to form a complex which is cleared from the circulation and the non-target spaces more rapidly than the primary antibody conjugate by itself. Preferably, the second antibody will be whole IgG or IgM. If the primary antibody is a fragment of IgG or IgM, it is preferable that the second antibody be whole IgG or IgM so that the primary/secondary complex retains the capability of activating the complement cascade. Conversely, where the primary antibody is whole IgG, the second antibody may be a fragment if the complex still retains complement-fixing capability. It is preferred that at least one of the primary/secondary pair be whole IgG or IgM. One advantage of using IgM is that it forms a higher molecular weight complex with primary antibody or with detached conjugates, ie., diagnostic and/or therapeutic principles such as drugs, chelating agents, radionuclides, and the like. This will increase the rate and effectiveness of clearance of non-target primary antibody and/or principle, especially from blood. The second antibody can be prepared by methods disclosed in the aforementioned Goldenberg '846 patent. Monoclonal anti-species IgG is also available and is advantageously used as second antibody in the present process. Non-metallic conjugates, e.g., radioiodinated linking groups or organic paramagnetic species such as nitroxides, can also be haptens to which the second antibody is specific.

The second antibody is injected into the subject after a sufficient time has elapsed following parenteral administration of the primary antibody-agent conjugate to permit maximum uptake thereof by leukocytes, typically about 2–72 hours following the initial administration, preferably at about 24–48 hours post-administration. If the primary antibody is not administered intravenously, it may be advantageous to administer at least a portion of the second antibody by the same parenteral route. It is advantageous however, to inject at least a portion of the second antibody intravenously to accelerate clearance of primary antibody which has diffused into the circulatory system.

The use of second antibody to clear circulating labeled primary antibody and enhance the localization ratio of the primary antibody is further enhanced by utilization of image-enhancing subtraction techniques as disclosed in the foregoing Goldenberg patents as well as the references cited therein. This is an art-recognized technique wherein an indifferent antibody or fragment labeled with a radionuclide capable of independent detection. This antibody has substantially the same kinetics of distribution and metabolism as the primary antibody during the period required for imaging. The injection of such antibodies is preferred over conventional subtraction agents, such as Tc-99m-labeled serum albumin, which are nevertheless suitable for use to enhance image processing by compensating for background. The use of the radiolabeled indifferent antibody as a subtraction agent permits computerized correction for nontarget background radiation from organs which effect clearance of antibodies from the circulatory system. It will be appreciated by those of ordinary skill in the art that the primary chimeric antibody and the indifferent antibody utilized as a subtraction agent are preferably from the same species or myeloma/hybridoma so that the second antibody will clear the primary monoclonal antibody and the indifferent antibody immunoglobulin from untargeted areas at substantially the same rate. It is further preferred that the second antibody be specific to a constant region of the primary and indifferent immunoglobulin species.

The amount of second antibody introduced will generally be that amount which can decrease the circulating primary antibody by 10–85% within 2–72 hours. The ratio of second antibody to primary antibody which will affect the clearance will depend upon the binding properties of the primary and secondary antibody pair. Preliminary screening of patient blood in vitro can be used to provide an initial estimate of the appropriate ratio. The screen will be used to determine the ratio of second antibody to primary antibody required to obtain a precipitin band in, e.g., a gel diffusion test. This indicates the general range of the molar ratio of second antibody to primary antibody, which serves as a measure of the lower limit for the ratio, since in vivo application may require a higher ratio of second antibody to primary antibody than is indicated by such in vitro tests.

In practice, the molar ratio of second antibody to primary antibody will generally be in the range of about 5–50, although the range should not be considered limitative. Molar ratios of second antibody to primary antibody of 15–25, and preferably 20–25, have been found to be advantageous where both the primary and the second antibody are whole IgG.

The chimeric antibody can be used to target a therapeutic agent to the site of infection or inflammation. Either a radioisotope or a drug/toxin can be so targeted. Suitable radioisotopes for therapy suitable for therapy will normally be beta-emitters, alpha-emitters and/or Auger electron-emitters, and include, but are not limited to, Copper-67, Iodine-125, Iodine-131, Rhenium 186, Rhenium 188, Bismuth-212, Astatine 211 and the like. Conjugates with these radioisotopes are prepared by analogous methods to imaging conjugates, by art-recognized techniques. They are most advantageously used for the treatment of infections that are resistant to drugs and that are sufficiently acute and debilitating to warrant the use of radiotherapy. Targeting according to the invention significantly increases the therapeutic index of the radiopharmaceutical compared to systemic treatment, and will justify this type of intervention where it could not be justified before.

Many drugs are known which have a cytotoxic effect on cells or microorganisms that may infect a human and cause a lesion. They can be found in any of the readily available art-recognized compendia of drugs and toxins, such as the Merck Index and the like. Any such antibiotic drug can be conjugated to a chimeric anti-leukocyte antibody to form a therapy agent according to the present invention, and the use of such a conjugate to improve the targeting of an antibotic drug to the site of an infectious lesion so as to increase its effective concentration at the site is a part of the present invention. One or more antibiotic drugs is/are conjugated to a polymeric carrier which is then conjugated to the chimeric antibody, for therapeutic use. In certain cases, it is possible to partially or completely detoxify a drug as part of the antibody conjugate, while it is in circulation, which can reduce systemic side effects of the drug and permit its use when systemic administration of the drug would be unacceptable. Administration of more molecules of the drug conjugated to a polymer which is further conjugated to the antibody, permits therapy while mitigating systemic toxicity.

The methodology of this invention is applicable to the therapeutic treatment of infectious lesions by conjugating the primary chimeric antibody to an antibiotic drug. Art recognized methods of conjugating antibiotic drugs to immunoglobulins are described, e.g., in: the chapter by O'Neill, entitled "The Use of Antibodies as Drug Carriers," in Drug Carriers in Biology and Medicine, G. Gregoriadis, ed., Academic Press London, 1979; Arnon et al., Recent Results in Cancer Res. 75:236, 1980; and Moolton et al., Immunolog. Res. 62:47, 1982, showing art awareness. These methods are quite similar to the methods employed for coupling drugs effective against various disease-causing microorganisms, such as against bacteria, viruses, fungi and diverse parasites to antibodies developed against these microorganisms, their products or antigens associated with their lesions.

Such antibaterial, antiviral, antiparasitic, antifungal and related drugs, e.g., sulfonamides, penicillins and cephalosporins, aminoglycosides, tetracyclines, chloramphenicol, piperazine, chloroquine, diaminopyridines, metroniazide, isoniazide, rifampins, streptomycins, sulfones, erythromycin, polymixins, nystatin, amphotericins, 5-fluorocytosine, 5-iodo-2'-deoxyuridine, 1-adamantanamine, adenine arabinoside, amanitins and azidothymidine (AZT), are preferred for coupling to appropriate specific antibodies/fragments and antibody/fragment composites. Various other potential antimicrobial agents for use in this invention are listed in Goodman et al., "The Pharmacological Basis of Therapeutics," Sixth Edition, A. G. Gilman et al., eds., Macmillan Publishing Co., New York, 1980, showing general art awareness. Various conditions appropriate and desirable for targeting drugs to specific target sites have been reviewed e.g. by Trouet et al., in Targeting of Drugs, G. Gregoriadis et al., eds., Plenum Press, New York and London, 1982, pp. 19–30, showing clinical knowledge of how such targeting would benefit patients suffering from infectious lesions.

The use of a second antibody as described above will increase the effectiveness of the therapeutic agent according to the invention in the same manner as for the diagnostic imaging conjugate. The effectiveness of the therapeutic agent is expressed in terms of its therapeutic index which, utilized in the conventional sense, is defined as the ratio of therapeutic effects to undesirable side effects. It is often defined in terms of a quantitative measure of efficacy vs. toxicity in a standard model system, e.g., the ratio of the median lethal dose ($LD_{50}$) to the median effective dose ($ED_{50}$). The use of second antibody as described herein produces an increase in the therapeutic index of anti-leukocyte chimeric antibody conjugates by clearing nontarget primary antibody and/or detached therapeutic principle. In addition to being specific to the primary chimeric antibody as discussed above, in the instance of the therapeutic preparation, the second antibody can be specific to the therapeutic agent. It can also be specific to a carrier for the therapeutic agent.

Therapeutic preparations contemplated herein comprise chimeric anti-leukocyte antibodies as defined above, conjugated to a therapeutically effective radioisotope or drug, in a suitable vehicle for parenteral administration. Therapeutic preparations may also include a separately packaged second antibody as described above. Suitable vehicles are well known in the art and can include, e.g., analogous sterile PBS solutions to those used for administration of diagnostic imaging agents, as discussed hereinabove.

The chimeric anti-leukocyte antibody imaging conjugates and therapeutic conjugates according to the invention also can be conveniently provided in a therapeutic or diagnostic kit for antibody targeting to an infectious or inflammatory lesion containing a focus of leukocytes. Typically, such a kit will comprise: a vial containing the chimeric antibody conjugate of the present invention, either as a lyophilized preparation or in an injection vehicle; if the conjugate is to be used for scintigraphic imaging or radioimmunotherapy, it will generally be provided as a cold conjugate together with reagents and accessories for radiolabeling, in separate containers, while MRI agents and therapeutic drug conjugates will generally be supplied with a paramagnetic species or an antibiotic already conjugated to the chimeric antibody. The kit may further contain a second, separately packaged, unlabeled antibody or antibody fragment specific against the chimeric antibody or the therapeutic agent, a carrier therefor, or a chelating agent for the radionuclide or paramagnetic ion.

The imaging preparations and methods of this invention are at least as efficacious as the conventional agents for determination of occult abscesses using In-111-labeled leukocytes and are clearly advantageous thereover in terms of cost, potential toxicity of the reagent, ease of use and, most significant, increased target specificity. The therapeutic reagents and methods of the invention provide a means to target sites of microbial infection with radioisotopes or antibiotic drugs to improve the therapeutic index of the radioisotopes or drugs, reduce systemic side effects and enhance their efficacy.

Without further elaboration, it is believed that one skilled in the art can, using the preceding description, utilize the present invention to its fullest extent. The following preferred specific embodiments are therefore, to be construed as merely illustrative, and not limitative of the remainder of the disclosure in any way whatsover. In the following examples, all temperatures are set forth uncorrected in degrees Celsius, unless otherwise indicated, all parts and percentages are by weight.

EXAMPLE 1

Chimeric Anti-leukocyte Antibody

A recombinant chimeric antibody is prepared by the method of Morrison et al., supra, from DNA isolated from a hybridoma producing a murine monoclonal antibody highly specific for granulocyte cells, and DNA encoding a human $IgG_1$ whose Fc portion has a high binding affinity for the Fc receptor of human monocytes.

The chimera is expressed in *E. coli* cells and isolated on an affinity column containing bound granulocytes.

The chimeric antibody is optionally conjugated to a chelator for a radioisotope or MRI enhancing agent, or otherwise treated with auxiliary reagents for conjugating such chelators or drug molecules to the antibody.

EXAMPLE 2

Scintigraphic Imaging Kit

A diagnostic imaging kit contains: a first sterile vial fitted with a rubber septum, and containing the lyophilizate of a solution of the chimeric antibody according to Example 1; optionally a second sterile (septum-sealed) vial containing a solution of a second antibody for rapid clearance of circulating labeled composite after localization, for example, affinity-purified rabbit anti-human IgG; and additional septum-sealed sterile vials and sterile syringes for labeling with, e.g., I-123, In-111 or Tc-99m-pertechnetate, and for injection of the labeled conjugate.

EXAMPLE 3

Diagnostic Imaging

A 30-year old female patient develops fever and abdominal pain one week after giving birth to a female infant by Caesarean section. The patient is maintained on I.V. antibiotic therapy for two weeks, but the fever and abdominal pain persists. CAT scans fail to demonstrate any abnormal mass. An immunoscintigraphy study is performed using the chimeric anti-granulocyte antibody of Example 1, directly labeled with I-123 radioisotope using the kit components of Example 2 especially adapted to conventional radioiodination and reactor-produced sodium iodide. An injection of 20 mCi of radiolabeled chimera is used, and the patient is scanned with a gamma camera in SPECT mode. The scan of the patient's abdomen demonstrates a focus of accumulation of I-123. Surgery is performed and an abscess is found at the site of I-123 activity. The abscess is drained, and pathology demonstrates large numbers of granulocytes, as well as monocytes, B-lymphocytes and activated T-lymphocytes, present in the purulent material. After two days, the patient's fever and pain subside.

EXAMPLE 4

Diagnostic Imaging

A 62-year old male patient that has been treated for pyelonephritis develops fever and acute spinal tenderness.

Vertebral osteomyelitis is suspected, but radiography of the spine is normal. An immunoscintigraphy study is performed using the chimeric antigranulocyte antibody of Example 1, directly labeled with Tc-99m radioisotope using the kit components of Example 2, wherein the chimeric antibody is conjugated to metallothionein terminal peptide and pretreated with stannous chloride, and generator-produced sodium pertechnetate. An injection of 20 mCi of radiolabeled chimera is used, and the patient is scanned with a gamma camera in planar imaging mode 24 hours after administration of the labeled conposite. The scan shows an intense focus of Tc-99m just above the point of termination of the spinal chord. Laminectomy and drainage of the epidural spaces is performed at the target site. Pathology of the purulent material in the drainage fluid demonstrates primarily exhuberant granulation tissue containing large numbers of mononuclear lymphoid cells with fewer numbers of granulocytes.

Use of the same chimera, conjugated to an aminodextran to which is bound an average of 100 modified diethylenetriaminepentaacetic acid (DTPA) chelators loaded with Gd(III) ions, is used in an MRI scan which also reveals the focus of inlammation as a clearly delineated epidural area contrasting with

EXAMPLE 5

Therapy

A 42-year old male with AIDS presents with bilateral pneumonia which fails to respond to conventional broad-spectrum antibiotic therapy. The clinical presentation and sputum cytology suggest Pneumocystis carinii pneumonia which appears to be advanced and to be causing the patient severe respiratory distress. The chimeric antibody of Example 1, which binds to a granulocyte antigen and to the Fc receptor of monocytes, is site-specifically conjugated to an average of one aminodextran carrier of about 15,000 MW, bearing an average of about 25 molecules of trimethoprin (Wellcome), a methotrexate derivative conjugated to the carrier by adapting the methodology of the Shih et al. patent cited hereinabove. A slow intravenous infusion of about 25 mg of the antibody conjugate delivers a therapeutic dose of the antibiotic to the pulmonary lesions, and is repeated on each of three successive days. Two days later, the patient begins to show improvement and his fever abates, and this is confirmed by improvement in his chest roentgenograms three days later. Most of the pneumonia resolves within two weeks of the antibody-drug conjugate treatment, with the patient receiving general supportive measures during this time.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for targeting an imaging or therapeutic agent to an inflammatory or infectious lesion, which comprises injecting a mammal parenterally with an effective amount for targeting of a chimeric antibody-agent conjugate comprising a chimeric antibody having an antigen-binding hypervariable region which binds specifically to granulocytes, and a constant region of a human immunoglobulin having an Fc portion with high affinity for receptors on human mononuclear lymphoid cells, said chimeric antibody being conjugated to at least one diagnostic or therapeutic agent.

2. The method of claim 1, wherein said conjugate is a diagnostic imaging conjugate and said chimeric antibody is conjugated to a diagnostic imaging agent.

3. The method of claim 2, wherein said imaging agent is a radioisotope, and wherein said method further comprises obtaining a scintigraphic image of said lesion after a time sufficient for said conjugate to localize at the site of said lesion.

4. The method of claim 2, wherein said imaging agent is a magnetic resonance image enhancing agent and wherein said method further comprises obtaining a magnetic resonance image of said lesion after a time sufficient for said conjugate to localize at the site of said lesion.

5. The method of claim 1, wherein said agent is a therapeutic agent.

6. The method of claim 5, wherein said therapeutic agent is a radioisotope.

7. The method of claim 6, wherein said radioisotope is Copper-67, Iodine-125, Iodine-131, Rhenium 186, Rhenium 188, Bismuth-212 or Astatine 211.

8. The method of claim 5, wherein said therapeutic agent is an antimicrobial agent.

9. The method of claim 1, additionally comprising the step of parenterally administering to said mammal, at a time after administration of said conjugate sufficient to permit maximum selective uptake thereof by leukocytes at the site of said lesion, a second, unlabeled antibody or antibody fragment which specifically binds to said conjugate, in an amount sufficient to increase the localization ratio of said conjugate by at least about 20 percent within a period of from 2 to 72 hours or to increase the therapeutic index of said therapeutic agent by at least about 10 percent.

* * * * *